US012327631B2

(12) United States Patent
Williams et al.

(10) Patent No.: US 12,327,631 B2
(45) Date of Patent: Jun. 10, 2025

(54) APPARATUS AND METHOD FOR UPDATING SOFTWARE IN A PATIENT SUPPORT APPARATUS USING A MEMORY TOGGLE

(71) Applicant: Hill-Rom Services, Inc., Batesville, IN (US)

(72) Inventors: Jason M. Williams, Cary, NC (US); Unnati Ojha, Apex, NC (US)

(73) Assignee: Hill-Rom Services, Inc., Batesville, IN (US)

( * ) Notice: Subject to any disclaimer, the term of this patent is extended or adjusted under 35 U.S.C. 154(b) by 1113 days.

(21) Appl. No.: 16/502,111

(22) Filed: Jul. 3, 2019

(65) Prior Publication Data

US 2020/0035358 A1 Jan. 30, 2020

Related U.S. Application Data

(60) Provisional application No. 62/711,102, filed on Jul. 27, 2018.

(51) Int. Cl.
*G16H 40/67* (2018.01)
*A61G 7/05* (2006.01)

(52) U.S. Cl.
CPC .............. *G16H 40/67* (2018.01); *A61G 7/05* (2013.01); *A61G 2203/12* (2013.01)

(58) Field of Classification Search
CPC ....... G16H 40/67; A61G 7/05; A61G 2203/12
See application file for complete search history.

(56) References Cited

U.S. PATENT DOCUMENTS

| 5,771,511 | A | 6/1998 | Kummer et al. |
|---|---|---|---|
| 7,319,386 | B2 | 1/2008 | Collins, Jr. et al. |
| 7,538,659 | B2 | 5/2009 | Ulrich et al. |
| 7,793,147 | B2 | 9/2010 | Stange et al. |
| 8,052,626 | B2 | 11/2011 | Huster et al. |
| 8,074,213 | B1 * | 12/2011 | Holtz .................. G06F 8/65 717/172 |
| 8,260,492 | B2 | 9/2012 | Stange et al. |

(Continued)

OTHER PUBLICATIONS

Extended European Search Report for European Patent Application No. 19186860.3 dated Nov. 29, 2019 (10 pages).

(Continued)

*Primary Examiner* — Wei Y Zhen
*Assistant Examiner* — Amir Soltanzadeh
(74) *Attorney, Agent, or Firm* — Barnes & Thornburg LLP

(57) ABSTRACT

An apparatus, system or method includes a patient bed for use with a network including a remote computer. The patient bed includes a bed frame to support a patient and bed circuitry carried by the bed frame. The bed circuitry is configured to receive a new version of bed operating software from the remote computer. The bed circuitry includes a first memory bank and a second memory bank. One of the first and second memory banks stores therein a current version of bed operating software. The other of the first and second memory banks stores therein the new version of bed operating software received from the remote computer. Thus, two versions of bed operating software are stored in the bed circuitry. A memory toggle is used to determine which version of the operating software in which of the two memory banks is used to operate the bed.

22 Claims, 5 Drawing Sheets

(56) References Cited

U.S. PATENT DOCUMENTS

| | | | |
|---|---|---|---|
| 8,572,778 B2 | 11/2013 | Newkirk et al. | |
| 9,513,899 B2 | 12/2016 | Collins, Jr. et al. | |
| 9,891,906 B1 | 2/2018 | Shen et al. | |
| 10,004,654 B2 | 6/2018 | Zerhusen et al. | |
| 2007/0174965 A1* | 8/2007 | Lemire | A61G 7/0528 |
| | | | 5/630 |
| 2007/0210917 A1* | 9/2007 | Collins, Jr. | G07C 3/00 |
| | | | 340/539.1 |
| 2009/0212925 A1 | 8/2009 | Schuman, Sr. et al. | |
| 2009/0212926 A1 | 8/2009 | Du et al. | |
| 2009/0217080 A1 | 8/2009 | Ferguson et al. | |
| 2010/0231421 A1 | 9/2010 | Rawls-Meehan | |
| 2012/0079473 A1* | 3/2012 | Watanabe | G06F 8/65 |
| | | | 717/170 |
| 2013/0305238 A1* | 11/2013 | Frayssignes | G06F 8/65 |
| | | | 717/173 |
| 2015/0033295 A1 | 1/2015 | Huster | |
| 2017/0060559 A1* | 3/2017 | Ye | G06F 8/65 |
| 2017/0124844 A1* | 5/2017 | Huster | A61G 7/0524 |
| 2017/0147322 A1* | 5/2017 | Vopni | G06F 8/65 |
| 2017/0323555 A1 | 11/2017 | Embree et al. | |
| 2018/0161225 A1* | 6/2018 | Zerhusen | A61G 7/05769 |
| 2018/0189049 A1* | 7/2018 | Madrid | G06F 21/575 |
| 2018/0214091 A1* | 8/2018 | Baker | A61B 5/746 |
| 2018/0270246 A1 | 9/2018 | Fukuda et al. | |
| 2019/0108012 A1* | 4/2019 | Rengarao Thyada | G06F 8/65 |
| 2020/0057704 A1* | 2/2020 | Bujan | G06F 8/656 |

OTHER PUBLICATIONS

Office Action in Chinese Patent Application No. 201910673423.2 dated Mar. 3, 2023 and its English translation; 28 pages.

Decision of Rejection for Chinese Patent Application No. 201910673423.2, dated Jan. 3, 2024, and its English translation (30 pages).

Chinese Office Action issued by the Chinese Patent Office for Chinese Patent Application No. 201910673423.2 dated Aug. 21, 2023, and its English translation (26 pages).

\* cited by examiner

APPARATUS AND METHOD FOR UPDATING SOFTWARE IN A PATIENT SUPPORT APPARATUS USING A MEMORY TOGGLE

The present application claims the benefit, under 35 U.S.C. § 119(e), of U.S. Provisional Application No. 62/711,102, filed Jul. 27, 2018, which is hereby incorporated by reference herein in its entirety.

BACKGROUND

The present disclosure relates to patient support apparatuses such as patient beds and particularly, to an apparatus, system and method for updating software of a patient support apparatus. More particularly, the present disclosure relates to transmitting updated software from a remote computer to multiple patient support apparatuses.

Patient support apparatuses such as patient beds found in healthcare facilities are sometimes upgraded with new operating software. The operating software is sometimes referred to as firmware. To upgrade the software of some patient support apparatuses, a service technician walks from bed-to-bed and physically connects a computer, such as a laptop or tablet computer, to the bed for replacement of the bed's current operating software with the new operating software. Some patient support apparatuses are able to have the operating software upgraded from a remote computer. See, for example, U.S. Pat. No. 9,513,899 in this regard. However, in the prior art, the patient support apparatuses are rendered inoperable during the software upgrade process while the existing or current version of the operating software is being overwritten with the new version of the operating software.

In some prior art systems, the software upgrade process can take up to twenty minutes to complete. During that time, any patients assigned to the beds being upgraded may need to be taken out of the respective beds, particularly if the bed has an air mattress which may deflate while the bed is inoperable. Furthermore, when the patient support apparatuses are being upgraded with new operating software by a remote computer, the caregiver at the remote computer needs to coordinate with other caregivers to identify which beds in which rooms are getting ready to have the software upgraded so the patients can be removed from the respective beds at the appropriate time. Accordingly, there is a need to improve the manner in which patient support apparatuses are upgraded with new versions of operating software.

SUMMARY

The present application discloses one or more of the features recited in the appended claims and/or the following features which, alone or in any combination, may comprise patentable subject matter:

A patient bed for use with a network including a remote computer may be provided and may include a bed frame to support a patient and bed circuitry that may be carried by the bed frame. The bed circuitry may be configured to receive a new version of bed operating software from the remote computer. The bed circuitry may include a first memory bank and a second memory bank. One of the first and second memory banks may store therein a current version of bed operating software. The other of the first and second memory banks may store therein the new version of bed operating software that may be received from the remote computer. Thus, two versions of bed operating software may be stored in the bed circuitry.

In some embodiments, the bed circuitry may be programmed with a memory toggle that may be used to select between the first and second memory banks thereby to select which version of bed operating software is used to operate the patient bed. The first and second memory banks each may include flash memory banks that are independent of each other. Alternatively or additionally, the memory toggle may include a toggle flag that may be used at start-up of the patient bed to determine which of the first and second memory banks is currently active.

It is contemplated by this disclosure that the new version of bed operating software received from the remote computer may be stored at download into whichever of the first and second memory banks may be inactive. Upon next start-up of the patient bed, the memory toggle may be switched so that the previously active memory bank becomes inactive and so that the previously inactive memory bank becomes active. If desired, during download of the new version of bed operating software into the inactive memory bank, the patient bed may continue to be operated according to the current version of bed operating software stored in the active memory bank.

Optionally, after the patient bed is operated according to the new version of the bed operating software, the bed circuitry may be programmed to automatically switch the memory toggle if an error occurs in the new version of bed operating software so that the prior version of bed operating software may once again be used to operate the patient bed. Alternatively or additionally, a user input may be carried by the frame and the user input may be usable to manually switch the memory toggle so that a user is able to select which of the software versions stored in the first and second memory banks is used to operate the patient bed. Further alternatively or additionally, the remote computer may be used to command the bed circuitry to switch the memory toggle to change which software version stored in the first and second memory banks is used to operate the patient bed.

According to another aspect of the present disclosure, a system may include a computer and a plurality of patient beds that may be remote from the computer. Each patient bed may include a bed frame to support a patient and bed circuitry that may be carried by the bed frame. The bed circuitry of each bed may be configured to receive a new version of bed operating software from the remote computer. The bed circuitry may include a first memory bank and a second memory bank. One of the first and second memory banks may store therein a current version of bed operating software for each bed. The other of the first and second memory banks may store therein the new version of bed operating software that may be received from the remote computer. Thus, two versions of bed operating software may be stored in the bed circuitry of each bed. If desired, the computer may be configured to upgrade the plurality of patient beds with the new version of bed operating software simultaneously.

In some embodiments, the computer may be configured to display each of the plurality of patient beds that may be available for upgrade. Alternatively or additionally, each of the patient beds that may be available for upgrade may register with the computer. Each of the patient beds that register with the computer may transmit a bed identification (ID) and a software version number of the current bed operating software for the respective patient bed.

Optionally, the computer may be configured to permit a user to select which of the plurality of patient beds is to be upgraded with the new version of bed operating software and to deselect others of the patient beds that are not to be upgraded. Further optionally, the bed circuitry of each patient bed may be programmed with a memory toggle that may be used to select between the first and second memory banks thereby to select which version of bed operating software is used to operate the respective patient bed. The first and second memory banks of each patient bed each may include flash memory banks that may be independent of each other.

In some embodiments, the memory toggle of each patient bed may include a toggle flag that mat be used at start-up of the respective patient bed to determine which of the first and second memory banks is currently active. The new version of bed operating software received from the remote computer by each patient bed may be stored at download into whichever of the first and second memory banks is inactive in the respective patient bed. Upon next start-up of each of the patient beds, the memory toggle may be switched so that the previously active memory bank becomes inactive and so that the previously inactive memory bank becomes active. During download of the new version of bed operating software into the inactive memory bank of each patient bed, each of the patient beds may continue to be operated according to the current version of bed operating software stored in the active memory bank of the respective patient bed.

If desired, after each of the patient beds is operated according to the new version of the bed operating software, the respective bed circuitry may be programmed to automatically switch the memory toggle if an error occurs in the new version of bed operating software so that the prior version of bed operating software is once again used to operate the respective patient bed. Alternatively or additionally, a user input may be carried by the frame of each patient bed. The respective user inputs may be usable to manually switch the memory toggle of the respective patient bed so that a user is able to select which of the software versions stored in the first and second memory banks of the respective bed may be used to operate the respective patient bed. Further alternatively or additionally, the remote computer may be used to command the bed circuitry to switch the memory toggle to change which software version stored in the first and second memory banks is used to operate the patient bed.

According to a further aspect of the present disclosure, a method may include providing a patient bed that may have a bed frame to support a patient, providing bed circuitry that may be carried by the bed frame, storing current bed operating software in a first memory bank of the bed circuitry, and transmitting a new version of bed operating software from a remote computer to the bed circuitry for storage in a second memory bank of the bed circuitry. Thus, two versions of bed operating software may be stored in the bed circuitry according to the method.

In some embodiments, the method may further include providing the bed circuitry with a memory toggle that may be used to select between the first and second memory banks thereby to select which version of bed operating software may be used to operate the patient bed. The first and second memory banks each may comprise flash memory banks that are independent of each other, for example. Alternatively or additionally, the memory toggle may include a toggle flag that may be used at start-up of the patient bed to determine which of the first and second memory banks is currently active. Further alternatively or additionally, the method includes using a memory toggle at the remote computer to command the bed circuitry to switch between the first and second memory banks thereby to select which version of bed operating software is used to operate the respective patient bed.

In some instances, the second memory bank may be inactive when the new version of bed operating software is received from the remote computer. The method may further include switching the memory toggle upon next start-up of the patient bed so that the previously active memory bank becomes inactive and so that the previously inactive memory bank becomes active. The method may also include continuing to operate the patient bed according to the current version of bed operating software during download of the new version of bed operating software into the inactive memory bank.

Optionally, the method may further include, after the patient bed is operated according to the new version of the bed operating software, automatically switching the memory toggle if an error occurs in the new version of bed operating software so that the prior version of bed operating software may once again be used to operate the patient bed. Alternatively or additionally, the method may further include using a user input carried by the frame to manually switch the memory toggle to select which of the software versions stored in the first and second memory banks may be used to operate the patient bed.

According to still another aspect of the present disclosure, a method may include providing a computer and providing a plurality of patient beds that may be remote from the computer. Each patient bed may include a bed frame to support a patient and bed circuitry that may be carried by the bed frame. The method may further include storing current bed operating software in a first memory bank of the bed circuitry of each of the patient beds and transmitting a new version of bed operating software from the remote computer to the bed circuitry for storage in a second memory bank of the bed circuitry of each of the patient beds. Thus, two versions of bed operating software may be stored in the bed circuitry of each of the patient beds.

In some embodiments, the method may further include displaying each of the plurality of patient beds that may be available for upgrade on a display screen of the remote computer. If desired, the method may further include registering each of the patient beds that may be available for upgrade with the computer. The method may also include transmitting to the remote computer a bed identification (ID) and a software version number of the current bed operating software from each of the patient beds that may register with the remote computer. Optionally, the method may further include selecting with the remote computer which of the plurality of patient beds may be upgraded with the new version of bed operating software and deselecting with the computer others of the patient beds that are not to be upgraded.

It is contemplated by this disclosure that the method may further include using a memory toggle of each patient bed to select between the first and second memory banks thereby to select which version of bed operating software is used to operate the respective patient bed. The first and second memory banks of each patient bed each may include flash memory banks that are independent of each other. Alternatively or additionally, the memory toggle of each patient bed may include a toggle flag that may be used at start-up of the respective patient bed to determine which of the first and second memory banks may be currently active.

In some embodiments, the new version of bed operating software that may be received from the remote computer by each patient bed may be stored at download into whichever of the first and second memory banks may be inactive in the respective patient bed. The method may further include upon next start-up of each of the patient beds, automatically switching the memory toggle so that the previously active memory bank may become inactive and so that the previously inactive memory bank may become active for each of the patient beds. Optionally, the method may further include continuing to operate the patient bed according to the current version of bed operating software during download of the new version of bed operating software into the inactive memory bank.

Optionally, the method may further include, after each patient bed is operated according to the new version of the bed operating software, automatically switching the memory toggle if an error occurs in the new version of bed operating software so that the prior version of bed operating software may once again be used to operate the respective patient bed. Alternatively or additionally, the method may further include using a user input that may be carried by the frame to manually switch the memory toggle to select which of the software versions stored in the first and second memory banks may used to operate the patient bed.

Additional features, which alone or in combination with any other feature(s), such as those listed above and/or those listed in the claims, may comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

The detailed description particularly refers to the accompanying figures, in which.

DETAILED DESCRIPTION

Figure 1:
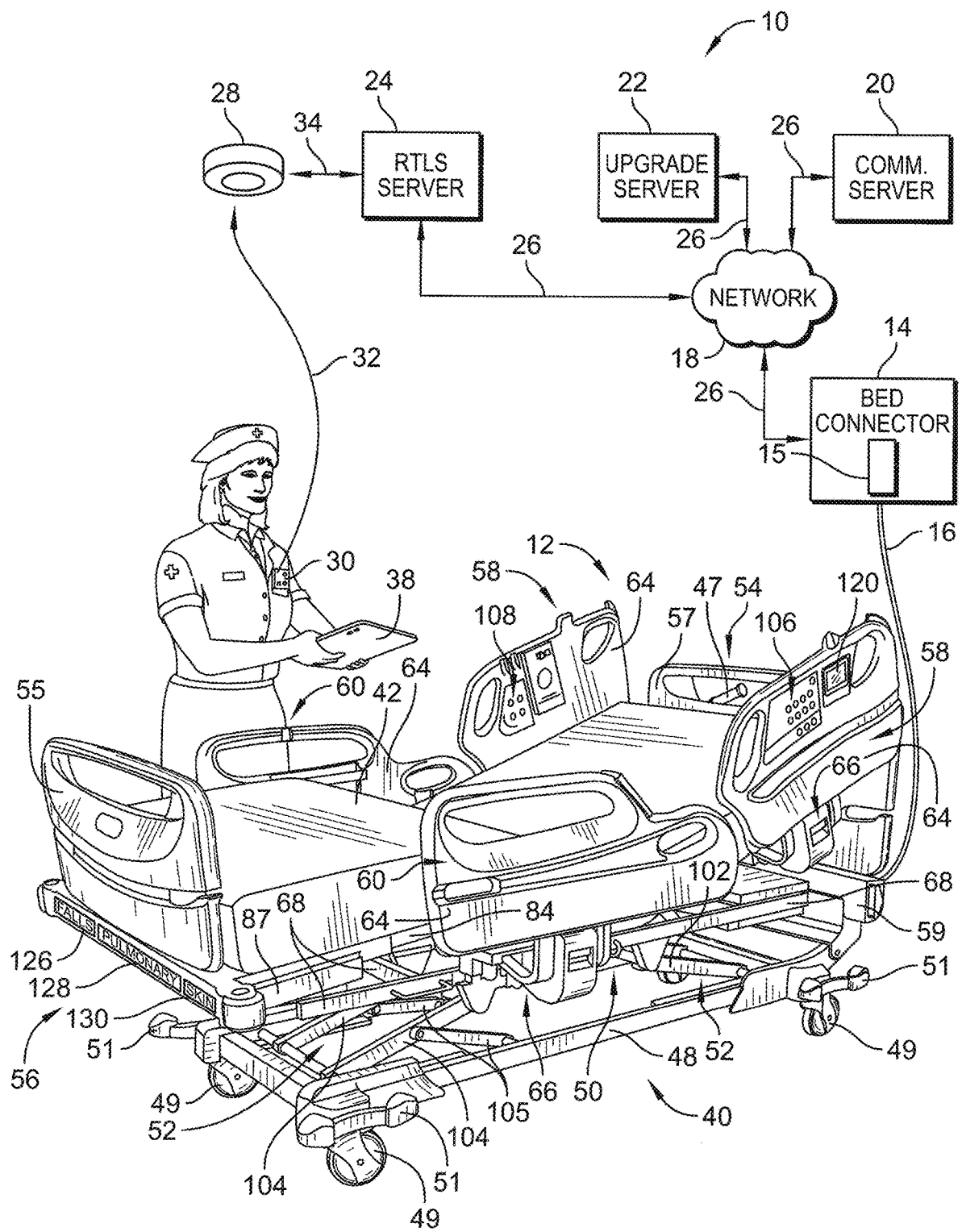
FIG. 1 is a diagrammatic view of a bed operating software upgrade system showing a patient bed coupled to a network via a bed connector; the bed being in communication with an upgrade server, a communication server, and a real time locating system (RTLS) server via the network; and a receiver of the RTLS being coupled to the RTLS server and in communication with a locating badge carried by a caregiver that is located alongside the patient bed.

A bed operating software upgrade system 10 includes a plurality of patient beds 12, only one of which is shown in FIG. 1, coupled to a network 18 of a healthcare facility such as a hospital, outpatient care facility, nursing home, and the like. In the illustrative example, patient bed 12 is coupled to network 18 via a bed connector unit 14 in the respective patient room. Illustratively, bed 12 is coupled to unit 14 with a cable 16 such as a cable having 37-pin connectors at its opposite ends as is known in the art. In other embodiments, a wireless connection is made between bed 12 and unit 14. Examples of suitable units 14 for use with bed 12 include bed interface units (BIU's), network interface unit (NIU's), and wireless interface unit (WIU's) available from Hill-Rom Company, Inc. of Batesville, Indiana.

Further details of BIU's and NIU's are shown and described in U.S. Pat. Nos. 7,538,659 and 7,319,386 and in U.S. Patent Application Publication Nos. 2009/0217080 A1, 2009/0212925 A1 and 2009/0212926 A1, each of which is hereby expressly incorporated by reference herein to the extent not inconsistent with this disclosure which shall control as to any inconsistencies. Further details of WIU's are shown and described in U.S. Patent Application Publication No. 2007/0210917 A1 which is also hereby expressly incorporated by reference herein to the extent not inconsistent with this disclosure which shall control as to any inconsistencies. Other types of bed connector units 14 are also within the scope of this disclosure including, but not limited to, a communications hub (aka "Universal Collector") shown and described in U.S. Patent Application Publication No. 2017/0323555 A1 and which is hereby incorporated herein by reference herein to the extent not inconsistent with this disclosure which shall control as to any inconsistencies. Therefore, the bed connector unit 14 shown in FIG. 1 is intended to represent all types of connectors that are used to receive bed status data from bed 12 and to communicate data from one or more other computer devices to bed 12 within a network 18.

Figure 2:
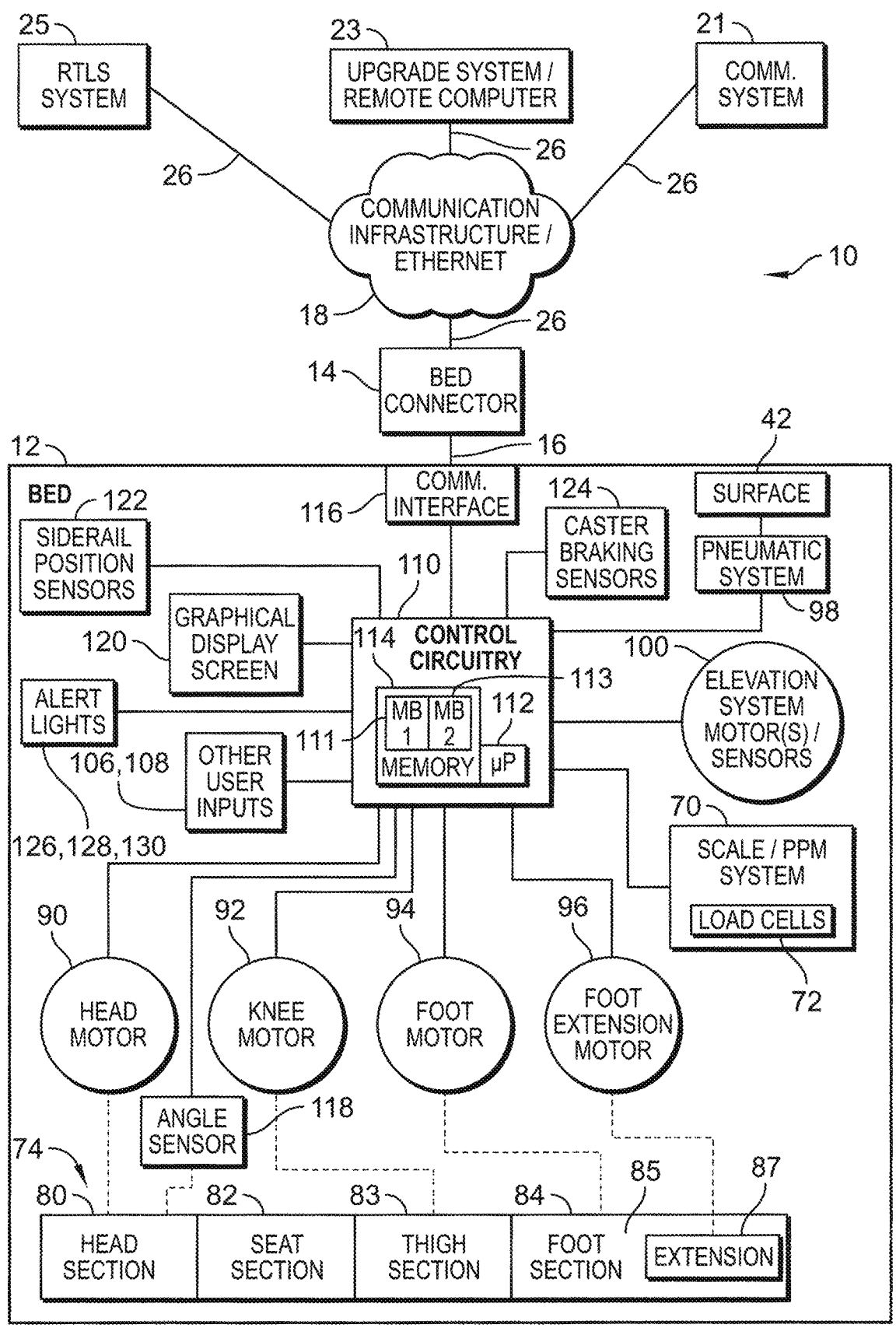
FIG. 2 is a block diagram showing various components of the patient bed and the bed operating software upgrade system.

As shown diagrammatically in FIGS. 1 and 2, a communication server 20 of a corresponding communication system 21, an upgrade server 22 of a corresponding upgrade system 23, and a real time locating system (RLTS) server 24 of a corresponding RTLS 25 are each coupled to network 18. Double headed arrows 26 in FIG. 1 represent the bidirectional communication links between network 18, unit 14 (and the corresponding bed 12) and each of servers 20, 22, 24 and therefore, with each other. Communication links 26 include wired communication links or wireless communication links at the option of the designer of system 10 in any given healthcare facility. Thus, in some embodiments, bed connector 14 includes wireless communication circuitry 15. Circuitry 15 communicates wirelessly with patient bed 12 and/or with network 18 such as through a wireless access point (WAP)(not shown) of network 18. Such wireless communication contemplated by this disclosure includes Bluetooth (BT), Bluetooth Low Energy (BLE), Zigbee, Z-Wave, and WiFi (e.g., any of the 802.11x protocols). However, it should be understood that all types of wireless communication are within the scope of the present disclosure, including infrared (IR) communications, ultrasonic (US) communications, ultra-wideband (UWB) communications, and so forth. In some embodiments in which bed 12 communicates wirelessly with bed connector 14, cable 16 is omitted.

The RTLS 25 of system 10 includes wireless transceiver units 28 placed throughout the healthcare facility. Only one such unit 28 is depicted diagrammatically in FIG. 1. The RTLS 25 of system 10 also includes caregiver locating or tracking tags or badges 30 that are worn by caregivers. Each of the transceiver units 28 receives a wireless signal from the badges 30 of each of the caregivers wearing badges 30 and that are within communication range of the respective unit 28 as indicated diagrammatically by arrow 32 in FIG. 1. The wireless signal from each badge 30 includes badge identification data (ID) which is unique to the corresponding badge 30. Unit 28 then transmits its ID, which corresponds to a particular location in the healthcare facility, and the badge (ID) to RTLS server 24 as indicated diagrammatically by a bidirectional communication link 34 in FIG. 1. Based on the received badge ID and the location ID from unit 28, server 24 determines the location of the caregiver within the healthcare facility. The location of assets such as beds 12 is tracked in a similar manner by server 24, in some embodiments, by attaching asset tags that are substantially the same as badges 30 to the assets to be tracked. In FIG. 1, the caregiver is shown carrying a tablet computer 38 which is configured to communicate wirelessly with other devices of network 18.

The present disclosure is primarily focused on updating or upgrading beds 12 with new operating software from server 22. The terms "upgrade" and "update" and other forms thereof (e.g., "upgrading" and "updating") are used interchangeably herein. Upgraded or updated operating software is intended to refer to new software for the patient support apparatus 12 to which it is sent, without regard to whether the new operating software is better than the prior version of the operating software in any respect. Server 22 is configured to upgrade the software of multiple beds 12 simultaneously as will be discussed in further detail below. To provide context to the types of features and functions to which bed operating software pertains, a discussion is provided below of the basic components and operation of various features of bed 12. It should be understood, however, that the particulars of any given version of software (e.g., the actual software code, itself) is not needed in order to understand the present disclosure. That is, bed operating software is the software that is executed to operate various electronic features and functions of bed 12.

Bed 12 includes a patient support structure such as a frame 40 that supports a surface or mattress 42 as shown in FIG. 1. It should be understood that FIG. 1 shows some details of one possible bed 12 having one particular configuration. However, this disclosure is applicable to other types of patient support apparatuses 12 having other configurations, including other types of beds, surgical tables, examination tables, stretchers, chairs, wheelchairs, patient lifts and the like.

Still referring to FIG. 1, frame 40 of bed 12 includes a base frame 48 (sometimes just referred herein to as a base 48), an upper frame assembly 50 and a lift system 52 coupling upper frame assembly 50 to base 48. Lift system 52 is operable to raise, lower, and tilt upper frame assembly 50 relative to base 48. Bed 12 has a head end 54 and a foot end 56. Patient bed 12 further includes a footboard 55 at the foot end 56 and a headboard 57 at the head end 54. Illustrative bed 12 includes a pair of push handles 47 coupled to an upstanding portion 59 of base 48 at the head end 54 of bed 12. Only a portion of one push handle 47 can be seen in FIG. 1. Headboard 57 is coupled to upstanding portion 59 of base as well. Footboard 55 is coupled to upper frame assembly 50. Base 48 includes wheels or casters 49 that roll along floor (not shown) as bed 12 is moved from one location to another. A set of foot pedals 51 are coupled to base 48 and are used to brake and release casters 49.

Illustrative patient bed 12 has four siderail assemblies coupled to upper frame assembly 50 as shown in FIG. 1. The four siderail assemblies include a pair of head siderail assemblies 58 (sometimes referred to as head rails) and a pair of foot siderail assemblies 60 (sometimes referred to as foot rails). Each of the siderail assemblies 58 and 60 is movable between a raised position, as shown in FIG. 1, and a lowered position (not shown). Siderail assemblies 58, 60 are sometimes referred to herein as siderails 58, 60. Each siderail 58, 60 includes a barrier panel 64 and a linkage 66. Each linkage 66 is coupled to the upper frame assembly 50 and is configured to guide the barrier panel 64 during movement of siderails 58, 60 between the respective raised and lowered positions. Barrier panel 64 is maintained by the linkage 66 in a substantially vertical orientation during movement of siderails 58, 60 between the respective raised and lowered positions.

Upper frame assembly 50 includes various frame elements 68 that form, for example, a lift frame and a weigh frame supported with respect to the lift frame by a set of load cells 72 of a scale and/or patient position monitoring (PPM) system 70 of bed 12. A patient support deck 74, shown diagrammatically in FIG. 2, is carried by the weigh frame portion of upper frame assembly 50 and supports mattress 42 thereon. Operation of the scale/PPM system 70 is among the features of bed 12 controlled by the bed operating software.

Patient support deck 74 includes a head section 80, a seat section 82, a thigh section 83 and a foot section 84 in the illustrative example as shown diagrammatically in FIG. 2. Sections 80, 83, 84 are each movable relative to the weigh frame portion of upper frame assembly 50. For example, head section 80 pivotably raises and lowers relative to seat section 82 whereas foot section 84 pivotably raises and lowers relative to thigh section 83. Additionally, thigh section 83 articulates relative to seat section 82. Also, in some embodiments, foot section 84 is extendable and retractable to change the overall length of foot section 84 and therefore, to change the overall length of deck 74. For example, foot section 84 includes a main portion 85 and an extension 87 in some embodiments as shown diagrammatically in FIG. 2.

In the illustrative embodiment, seat section 82 is fixed in position with respect to the weigh frame portion of upper frame assembly 50 as patient support deck 74 moves between its various patient supporting positions including a horizontal position to support the patient in a supine position, for example, and a chair position (not shown) to support the patient in a sitting up position. In other embodiments, seat section 82 also moves relative to upper frame assembly 50, such as by pivoting and/or translating. Of course, in those embodiments in which seat section 82 translates relative to the upper frame assembly 50, the thigh and foot sections 83, 84 also translate along with seat section 82. As bed 12 moves from the horizontal position to the chair position, foot section 84 lowers relative to thigh section 83 and shortens in length due to retraction of the extension 87 relative to main portion 85. As bed 12 moves from the chair position to the horizontal position, foot section 84 raises relative to thigh section 83 and increases in length due to extension of the extension 87 relative to main portion 85.

Thus, in the chair position, head section 80 extends upwardly from upper frame assembly 50 and foot section 84 extends downwardly from thigh section 83.

As shown diagrammatically in FIG. 2, bed 12 includes a head motor or actuator 90 coupled to head section 80, a knee motor or actuator 92 coupled to thigh section 83, a foot motor or actuator 94 coupled to foot section 84, and a foot extension motor or actuator 96 coupled to foot extension 87. Motors 90, 92, 94, 96 may include, for example, an electric motor of a linear actuator. In those embodiments in which seat section 82 translates along upper frame assembly 50 as mentioned above, a seat motor or actuator (not shown) is also provided. Head motor 90 is operable to raise and lower head section 80, knee motor 92 is operable to articulate thigh section 83 relative to seat section 82, foot motor 94 is operable to raise and lower foot section 84 relative to thigh section 83, and foot extension motor 96 is operable to extend and retract extension 87 of foot section 84 relative to main portion 85 of foot section 84. Operation of motors 90, 92, 94, 96 is among the features of bed 12 controlled by the bed operating software.

In some embodiments, bed 12 includes a pneumatic system 98 that controls inflation and deflation of various air bladders or cells of mattress 42. The pneumatic system 98 is represented in FIG. 2 as a single block but that block 98 is intended to represent one or more air sources (e.g., a fan, a blower, a compressor) and associated valves, manifolds, air passages, air lines or tubes, pressure sensors, and the like, as well as the associated electric circuitry, that are typically included in a pneumatic system for inflating and deflating air bladders of mattresses. Operation of pneumatic system 98 is among the features of bed 12 controlled by the bed operating software.

As also shown diagrammatically in FIG. 2, lift system 52 of bed 10 includes one or more elevation system motors or actuators 100, which in some embodiments, comprise linear actuators with electric motors. Thus, actuators 100 are sometimes referred to herein as motors 100 and operation of the motors 100 is among the features of bed 12 controlled by the bed operating software. Alternative actuators or motors contemplated by this disclosure include hydraulic cylinders and pneumatic cylinders, for example. The motors 100 of lift system 52 are operable to raise, lower, and tilt upper frame assembly 50 relative to base 48. In the illustrative embodiment, one of motors 100 is coupled to, and acts upon, a set of head end lift arms 102 and another of motors 100 is coupled to, and acts upon, a set of foot end lift arms 104 to accomplish the raising, lowering and tilting functions of upper frame 50 relative to base 48. Guide links 105 are coupled to base 48 and to lift arms 104 in the illustrative example as shown in FIG. 1. Illustrative bed 12 of FIG. 1 is the CENTRELLA™ bed available from Hill-Rom Company, Inc. Other aspects of illustrative bed 12 are shown and described in more detail in U.S. Patent Application Publication No. 2018/0161225 A1 which is hereby expressly incorporated by reference herein to the extent not inconsistent with the present disclosure which shall control as to any inconsistencies.

Each of siderails 58 includes a first user control panel 106 coupled to the outward side of the associated barrier panel 64. Controls panels 106 include various buttons that are used by a caregiver to control associated functions of bed 12. For example, control panel 106 includes buttons that are used to operate head motor 90 to raise and lower the head section 80, buttons that are used to operate knee motor 92 to raise and lower the thigh section 83, and buttons that are used to operate motors 100 to raise, lower, and tilt upper frame assembly 50 relative to base 48. In some embodiments, control panel 106 also includes buttons that are used to operate motor 94 to raise and lower foot section 84 and buttons that are used to operate motor 96 to extend and retract foot extension 87 relative to main portion 85. Each of siderails 58 also includes a second user control panel 108 coupled to the inward side of the associated barrier panel 64. Controls panels 108 include various buttons that are used by a patient to control associated functions of bed 12. In some embodiments, the buttons of control panels 108, 108 comprise membrane switches that are used to control head motor 90 and knee motor 92.

As shown diagrammatically in FIG. 2, bed 12 includes control circuitry 110 that is electrically coupled to motors 90, 92, 94, 96 and to motors 100 of lift system 52. Control circuitry 110 is represented diagrammatically as a single block in FIG. 2, but control circuitry 110 in some embodiments, comprises various circuit boards, electronics modules, and the like that are electrically and communicatively interconnected. Control circuitry 110 includes one or more microprocessors 112 or microcontrollers that execute software to perform the various control functions and algorithms described herein. Thus, circuitry 110 also includes memory 114 for storing software, variables, calculated values, and the like as is well known in the art.

According to the present disclosure, memory 114 of circuitry 110 includes a first memory bank 111 and a second memory bank 113 which are dedicated for the storage of two versions of bed operating software. Thus, memory bank 111 stores a first version of bed operating software and memory bank 113 stores a second version of bed operating software. However, as will be discussed in further detail below, only of memory banks 111, 113 is active at any given instance in time, with the other memory bank 113 being inactive. In some embodiments, memory banks 111, 113 comprise flash memory banks that are independent of each other. That is, when memory bank 111 is active, none of the software in memory bank 113 will be used, and when memory bank 113 is active, none of the software in memory bank 111 will be used. In some embodiments, memory banks 111, 113 are included in separate integrated circuit chips, such as EEPROM's, EPROM's, and the like. In other embodiments, memory banks 111, 113 are included on the same integrated circuit chip but there is a dedicated block of memory addresses for each memory bank 111, 113.

As shown diagrammatically in FIG. 2, a user inputs block represents the various user inputs such as buttons of control panels 106, 108, for example, that are used by the caregiver or patient to communicate input signals to control circuitry 110 of bed 12 to command the operation of the various motors 90, 92, 94, 96, 100 of bed 12, as well as commanding the operation of other functions of bed 12. Bed 12 includes at least one graphical user input (GUI) or display screen 120 coupled to a respective siderail 58 as shown in FIG. 1. Display screen 120 is coupled to control circuitry 110 as shown diagrammatically in FIG. 2 and may be a touchscreen display, for example. In some embodiments, two graphical user interfaces 120 are provided and are coupled to respective siderails 58. Alternatively or additionally, one or more graphical user interfaces are coupled to siderails 60 and/or to one or both of the headboard 57 and footboard 55.

In the illustrative embodiment, bed 12 has a communication interface or port 116 which provides bidirectional communication via cable 16 with bed connector 14 which, in turn, communicates bidirectionally with network 18 and the various computers and systems of network 18, such as illustrative servers or computers 21, 23, 25. In other embodiments, communication interface 116 is used for wireless communications with bed connector 14. Communication interface 116 also may be configured for wireless communication with network 18 and its associated devices without the use of bed connector 14 in some embodiments. For example, WiFi communications between communication interface 116 and one or more WAP's of network 18 is contemplated by this disclosure. The communication data to and from interface 116 is among the features of bed 12 controlled by the bed operating software.

Still referring to FIG. 2, bed 12 includes various sensors to sense the states or positions of various portions of bed 12. In the illustrative example, bed 12 includes an angle sensor 118 coupled to head section 80 to sense an angle of head section elevation (sometimes referred to as the head-of-bed (HOB) angle). Angle sensor 118 is an accelerometer (single-axis or multi-axis) in some embodiments. In such embodiments, the HOB angle is measured with respect to a horizontal reference axis and/or with respect to a vertical reference axis depending upon the orientation of the accelerometer relative to head section 80 and depending upon the type of accelerometer. In other embodiments, angle sensor 118 includes a rotary potentiometer which measures the HOB angle between head section 90 and another portion of frame 40 such as one of frame members 68 of upper frame assembly 50. In further embodiments, angle sensor 90 is included in head motor 90 and has an output that correlates to the HOB angle. Motor 90 may include, for example, a shaft encoder, a Hall effect sensor, a rotary potentiometer, or some other sensor which serves as angle sensor 118 of bed 12 in such embodiments. Similar such sensors are included in elevation system motors 100 in some embodiments and are used to determine the position of upper frame assembly 50 relative to base 48 such as the height of upper frame assembly 50 and/or amount of tilt of upper frame assembly 50 relative to base 48.

Bed 12 also includes siderail position sensors 122 to sense the position (e.g., raised and/or lowered) of each of siderails 58, 60 and one or more caster braking sensors 124 to sense whether casters 49 are braked or released. In some embodiments, sensors 122, 124 include limit switches that are engaged or disengaged by a linkage mechanism, such as linkage 66 in the case of siderails 58, 60, to produce output signals indicative of the position of the respective mechanical structure. Alternatively, Hall effect sensors may be used as some or all of sensors 122, 124 in some embodiments. The foregoing types of sensors 122, 124 are just a couple examples of suitable sensors and therefore, this disclosure is intended to cover all types of sensors that may be used as sensors 122, 124. Each of the sensors mentioned above, including sensors internal to motors 100 and sensors 118, 122, 124 are each coupled electrical to control circuitry 110 for analysis and/or processing. Thus, data from sensors 118, 122, 124 is used by the bed operating software in connection with the control and operation of various features of bed 12.

In some embodiments, bed 12 has safety protocol capability. Thus, control circuitry 110 is programmed with the bed operating software to enable and disable the safety protocols of bed 12. It is within the scope of the present disclosure for the safety protocols to be enabled (aka "activated" or "turned on") and disabled (aka "deactivated" or "turned off") either remotely via a computer of network 18 or by use of user inputs 106, 108, 120 of bed 12. In some embodiments, control circuitry 110 of bed 12 is configured to implement three different safety protocols, namely, a falls risk protocol (aka a falls protocol), a pulmonary protocol, and a safe skin protocol (aka a skin protocol). It should be understood that these are just examples of possible protocols for implementation on bed 12 and other protocols based on bed status information are within the scope of this disclosure. The safety protocols are among the features of bed 12 to which the bed operating software pertains.

As shown in FIG. 1, bed 12 includes three status or alert lights at foot end 56 corresponding to the three protocols. Thus, bed 12 includes a falls alert light 126, a pulmonary alert light 128, and a skin alert light 130. In the illustrative example, alert lights 126, 128, 130 are coupled to a lateral frame member of extension 87 of foot section 84 and are situated beneath footboard 55. In other embodiments, alert lights 126, 128, 130 may be located elsewhere on bed 12 such as on base 48 and/or one or more of siderails 58, 60. In FIG. 2, alert lights 126, 128, 130 are represented diagrammatically as a single block and are coupled electrically to control circuitry 110 to control the manner in which alert lights 126, 128, 130 are illuminated as will be discussed in further detail below. In other embodiments, bed 12 is equipped with the alert lights discussed in U.S. Patent Application Publication No. 2018/0161225 A1 which is already incorporated by reference herein, in lieu of or in addition to alert lights 126, 128, 130.

In some embodiments, alert lights 126, 128, 130 are illuminated different colors to indicate certain statuses. For example, lights 126, 128, 130 are turned off if the particular protocol is not enabled, meaning the bed statuses contributing to the particular protocol are not being monitored for a protocol violation. Lights 126, 128, 130 are illuminated a first color, such as green for example, if the associated protocol is enabled, meaning the bed statuses contributing to the particular protocol are being monitored for a protocol violation, but all of the monitored bed statuses for the particular protocol are satisfactory or in a desirable state (i.e., not violated). Lights 126, 128, 130 are illuminated a second color, such as amber or yellow for example, if the associated protocol is enabled and at least one of the monitored bed statuses for the particular protocol is undesirable or unsatisfactory (i.e., violated).

In some embodiments, an audible alarm of bed 12 may also sound under the control of control circuitry 110 if an unsatisfactory condition of a particular protocol is detected. Lights 126, 128, 130 are illuminated a third color, such as blue for example, if the associated protocol is enabled and at least one of the monitored bed statuses for the particular protocol is undesirable (i.e., violated), but the alert has been suspended as will be discussed in further detail below. If the alert has been suspended, any associated audible alarms may be turned off during the alarm suspension. The operation of alert lights 126, 128, 130 and the audible alarm, if any, of bed 12 is among the features controlled by the bed operating software.

As mentioned above, illustrative bed 12 is configured to implement a falls risk protocol, a pulmonary protocol, and a safe skin protocol. According to the falls risk protocol example given herein, PPM system 70 is required to be enabled to monitor a position of the patient relative to the frame 40, upper frame assembly 50 of frame 40 is required to be in a lowest position relative to a base 48 of frame 40 as sensed by sensors of motors 100, siderails 58, 60 of the frame 40 are required to be in the respective raised positions as sensed by siderail position sensors 122, and the caster brake of one or more of casters 49 is required to be braked or set as sensed by caster braking sensors 124. Thus, if PPM system 70 indicates that the patient is moving toward exiting bed 12 by a threshold amount (including exiting the bed 12) such movement beyond the threshold is considered to be a violation of the falls protocol by control circuitry 110 assuming the falls protocol is enabled. Similarly, if upper frame assembly 50 is moved upwardly out of its lowest position, or if any of siderails 58, 60 are moved out of their raised positions, or if the one or more casters 49 are released or unbraked, each of those unwanted conditions is considered to be a violation of the falls protocol by the bed operating software of control circuitry 110 assuming the falls protocol is enabled.

According to the pulmonary protocol example given herein, head section 80 of mattress support deck 74 of frame 40 is required to be elevated above a threshold angle as measured by angle sensor 118. The threshold angle may be about 30 degrees, for example. In some embodiments, GUI 120 is used to adjust the threshold angle to an angle greater than 30 degrees (e.g., 45 degrees or 60 degrees) or to an angle less than 30 degrees (e.g., 17 degrees or 10 degrees). Thus, if the HOB angle falls below the threshold angle, that is considered to be a violation of the pulmonary protocol, assuming the pulmonary protocol is enabled. Having the HOB angle above a threshold angle, such as 30 degrees, helps to prevent ventilator assisted pneumonia (VAP) in some patients. Alternatively or additionally, the pulmonary protocol may require that the patient undergo certain pulmonary therapies performed by mattress 42 within certain time intervals. Examples of such pulmonary therapies include, for example, continuous lateral rotation therapy (CLRT) using rotation bladders of mattress 42 and/or percussion/vibration (P&V) therapy using P&V bladders of mattress 42. Thus, CLRT or P&V therapy may be required for ½ hour, 1 hour, 2 hours, etc. twice per day or at least once within in any 8 hour nursing shift according to the pulmonary protocol as monitored by the bed operating software, just to give a couple of nonlimiting examples.

According to the safe skin protocol example given herein, the patient is required to move relative to the frame 40 by a threshold amount so as not to be stationary for a threshold amount of time. Such movement is detected by the PPM system 70 in the illustrative embodiment. Alternatively or additionally, the safe skin protocol may require the operation of certain features of mattress 42 for certain periods of time or at certain intervals. For example, an alternating pressure feature of mattress 42 may be required to be operating substantially continuously while the patient is in bed 12. Alternating pressure refers to sequentially inflating and deflating every other laterally extending bladder of two sets of interleaved or interdigitated bladders of mattress 12. Alternatively or additionally, the safe skin protocol may require a microclimate management layer or low airloss topper of mattress 42 to have air circulated therethrough to remove or reduce the amount of moisture and/or heat between the patient and the upper surface of mattress 42. Further alternatively or additionally, the safe skin protocol may require that turn assist bladders of the mattress 42 be used from time to time to turn the patient to their left side and to their right side. When the safe skin protocol is enabled, the bed operating software of control circuitry 110 monitors the various time thresholds for patient movement, alternating pressure, microclimate management operation, and turn assist, as the case may be.

Figure 3:
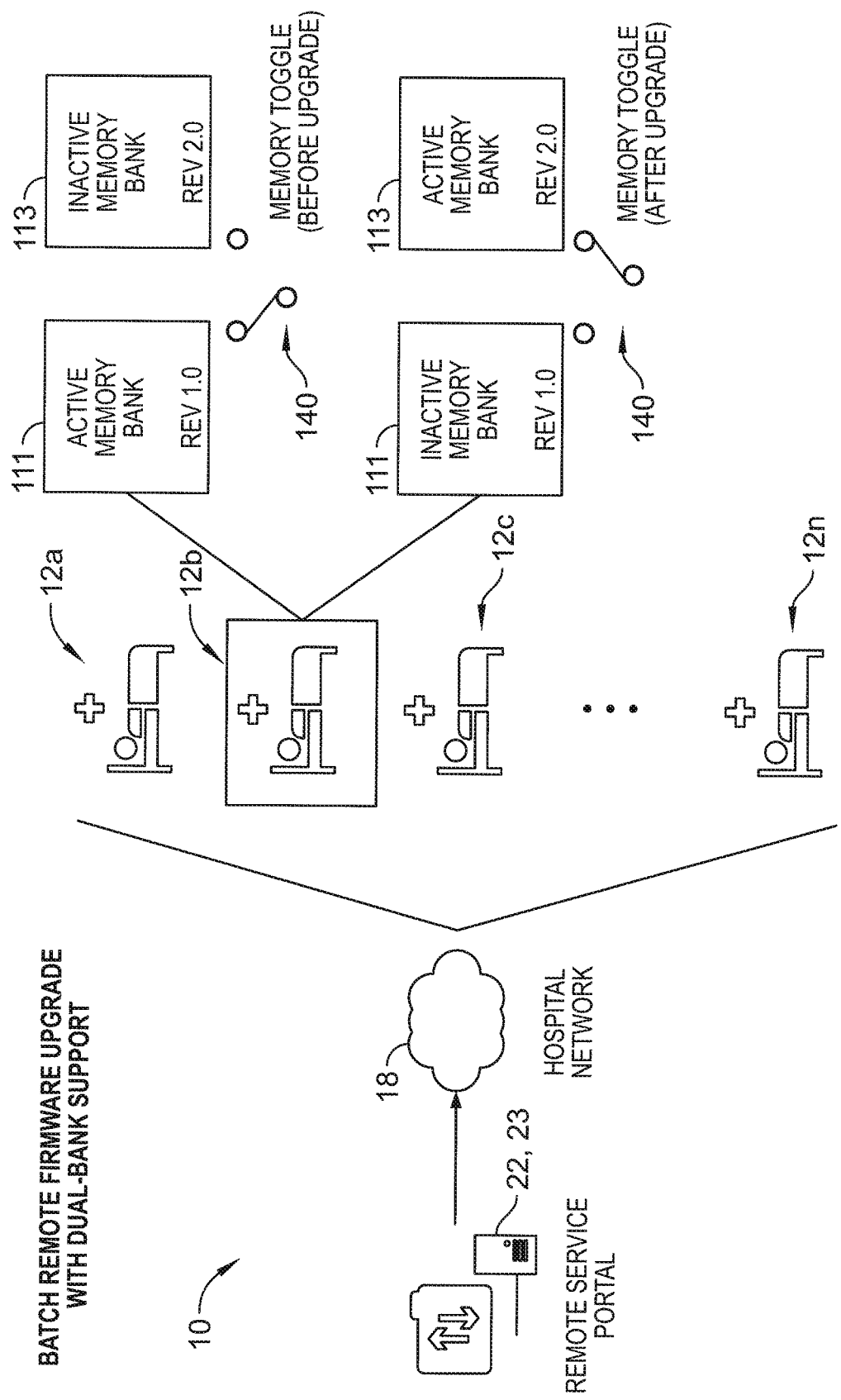
FIG. 3 is a diagrammatic view showing a plurality of the patient beds coupled to the network and showing one of the beds having a first memory bank that is active and a second memory bank that is inactive as determined by a first state of a memory toggle prior to a bed operating software upgrade and showing the memory toggle in a second state after the bed operating software upgrade so that the first memory bank is inactive and the second memory bank is active.

Referring now to FIG. 3, beds 12 are shown diagrammatically as bed 12a, bed 12b, bed 12c, and bed 12n. Vertical dashes between bed 12c and bed 12n indicate diagrammatically that system 10 may include any number of beds 12 that may be upgraded with new bed operating software from upgrade server 22 or remote computer of upgrade system 23 via network 18. Each bed 12a-12n includes a memory toggle 140 that indicates whether memory bank 111 or memory bank 113 is the active memory bank 111, 113 and which is the inactive memory bank 111, 113. In FIG. 3, bed 12b is shown with upper and lower enlarged depictions of memory banks 111, 113. In the upper depiction of memory banks 111, 113, the memory toggle 140 is in a first position having memory bank 111 being the active memory bank and having memory bank 113 being the inactive memory bank. Thus, the bed operating software (Rev. 1.0 in the illustrative example) of memory bank 111 is used to operate the features and functions of bed 12b before the software upgrade as indicated by the textual information provided in connection with the upper pair of memory banks 111, 113. In the lower depiction of memory banks 111, 113, the memory toggle 140 is in a second position having memory bank 113 being the active memory bank and having memory bank 111 being the inactive memory bank. Thus, the bed operating software (Rev. 2.0 in the illustrative example) of memory bank 113 is used to operate the features and functions of bed 12b after the software upgrade as indicated by the textual information provided in connection with the lower pair of memory banks 111, 113.

Memory toggle 140 is a toggle flag stored in a particular memory location of memory 114 outside of memory banks 111, 113 and is used at start-up (aka boot-up) to determine which of memory banks 111, 113 is to be the active memory bank that contains the bed operating software to be used to operate the bed 12 after start-up. The use of memory toggle 140 allows new bed operating software to be loaded onto the inactive memory bank 111, 113 while a prior version of bed operating software continues to be run on the active memory bank 111, 113. That is, bed 12 continues to operate according to the current version of bed operating software (Rev 1.0 in the illustrative example of FIG. 3) while the new operating software (Rev. 2.0 in the illustrative example of FIG. 3) is being loaded. This is an improvement over prior art systems, such as the one disclosed in U.S. Pat. No. 9,513,899, in which the bed 12 is rendered inoperable during the software upgrade process while the existing or current version of the operating software is being overwritten with the new version of the operating software.

Upon receiving the file transfer of the new bed operating software from the upgrade server 22 and/or computer 23, the microprocessor 112 of the respective bed 12 changes the binary state of the memory toggle 140 (e.g., toggle flag) to change the respective memory bank 111, 113 that is active. The memory toggle 140, therefore, includes a single bit in some embodiments and includes multiple bits (such as a word) in other embodiments. Thus, if memory bank 111 was previously active prior to the software upgrade, then memory bank 113 becomes the active memory bank after the software upgrade at next start-up or boot-up of the respective bed 12, and if memory bank 113 was previously active prior to the software upgrade, then memory bank 111 becomes the active memory bank after the software upgrade at the next start-up or boot-up of the respective bed 12. However, the previous version of bed operating software remains in whichever memory bank 111, 113 becomes the inactive memory bank 111, 113 after the software upgrade.

According to the present disclosure, therefore, two versions of bed operating software are stored in memory 114 of bed 12 at any given time, assuming the bed operating software has been upgraded at least once. Because of this, if an error of sufficient severity occurs in the new version of bed operating software in the active memory bank 111, 113, the memory toggle 140 is switched so that the prior version of bed operating software is, once again, used to operate the features and functions of the bed. Such an error is sometimes referred to herein as a "bed operating software malfunction error" or just "malfunction error" or some such similar term. The switching of the memory toggle 140 in response to such a malfunction error occurs automatically at the respective bed 12 in some embodiments. In such embodiments, memory 114 includes software outside of memory banks 111, 113 that is executed by processor 112 to determine whether to switch the memory toggle 140 to change the inactive memory bank 111, 113 to the active memory bank 111, 113 in response to the detected malfunction error.

In other embodiments, a user input such as one of inputs 106, 108 or an input accessible using graphical display screen 120 is selected or pressed by a caregiver on the respective bed 12 to switch the memory toggle 140 to change the inactive memory bank 111, 113 to the active memory bank 111, 113 after detection of an operating software malfunction error of sufficient magnitude in the current bed operating software. In such embodiments, a message or alert regarding the malfunction error is displayed on screen 120 and/or is transmitted to a wireless communication device, such as tablet computer 38, carried by an assigned caregiver and/or is displayed on a display screen of the upgrade server 22 and/or one remote upgrade computer 23 and/or on some other remote computer 23 such as a nurse call computer. Thus, in some embodiments, communication server 20 initiates a message to the caregiver's wireless communication device 38 in response to receiving a message originating from bed 12 that a bed operating software malfunction error has occurred in the active bed operating software.

Figure 4:
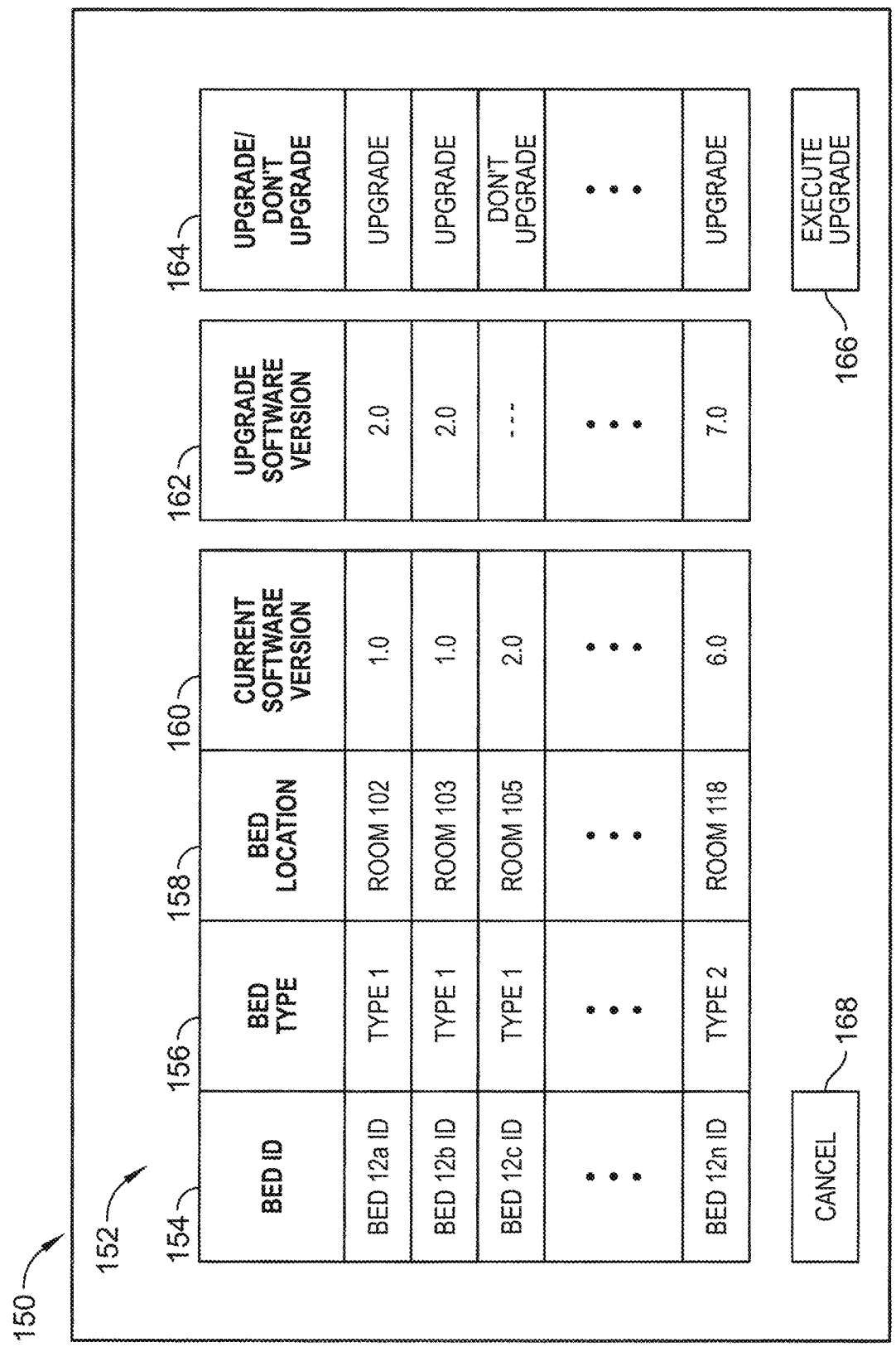
FIG. 4 is a screen shot of an upgrade computer screen showing a list of beds that are available for a software upgrade, showing a software version of the current bed operating software, and showing a set of selection icons or buttons for selecting which of the patient beds are to bed upgraded with new bed operating software.

Referring now to FIG. 4, an illustrative example of an upgrade computer screen 150 which appears on the display screen of the upgrade server 22 and/or remote upgrade computer 23 and which is used by a user to select the beds 12a-12n that are to be updated with new operating software is shown. Screen 150 includes a table 152 having a first column 154 that lists the bed identification codes (bed ID's) of the beds 12a-12n that are in communication with server 22, a second column 156 that lists the bed type of the beds 12a-12n that are in communication with server 22, a third column 158 that lists the location of each of beds 12a-12n that are in communication with server 22, and a fourth column 160 that lists the current version of software being operated in the active memory bank 111, 113 of the respective beds, regardless of whether the first memory bank 111 or the second memory bank 113 is the active memory bank.

Screen 150 also has a separate column 162 to the right of table 152 that lists the version of software that is available for upgrading or updating each bed 12a-12n in communication with server 22 and a separate Upgrade/Don't Upgrade column 164 to the right of column 162 that indicates, for each bed 12a-12n in table 152, whether the particular bed 12a-12n is to have its software updated to the new version of software shown in column 162. Each cell in column 164 can be selected by a user sequentially to toggle between the "Upgrade" and "Don't Upgrade" options. Thus, if a cell has the text "Upgrade" shown in it, then a subsequent selection of that cell will change the selection to "Don't Upgrade" and vice versa. If the display screen of the upgrade server 22 or computer 23 on which screen 150 is displayed is a touchscreen, then the user can simply touch each cell in column 164, as desired, to toggle between the "Upgrade" and "Don't Upgrade" options. Alternatively or additionally, the user can click on each cell in column 164 with a cursor controlled by a computer mouse, for example, or use arrow keys to move a cursor to the desired cell and then pressing an enter key, to toggle between the two options. It should be appreciated that column 164 may just as well use the terms "Update" and "Don't Update" or similar such terms, in lieu of the terms "Upgrade" and "Don't Upgrade."

In some embodiments, the list of beds appearing in table 152 includes those patient beds 12 that have registered with server 22 or remote computer 23. For example, each of the patient beds 12 that register with the server 22 or computer 23 transmits a bed identification (ID) and a software version number of the current bed operating software for the respective patient bed. The registration occurs, in some embodiments, when a new patient bed 12 is initially communicatively coupled to respective bed connector 14, for example. Server 22 communicates with server 24 in some embodiments to determine the location of the respective bed 12 if the bed 12 has an equipment tag (similar to badge 30 worn by the caregiver) that communicates with transceiver unit 28.

Screen 150 has an Execute Upgrade button or icon 166 that is selected by the user after the desired Upgrade/Don't Upgrade selections have been made in column 164 for each listed bed 12a-12n if the user wants to proceed with upgrading the bed operating software with the new version of software listed in column 162. In response to selection of button 166, server 22 transmits to each bed 12a-12n having the "Upgrade" option selected in column 164, the version of bed operating software listed in column 162 for that particular bed 12a-12n. Thus, the beds 12a-12n having the "Upgrade" option selected are upgraded with new bed operating software simultaneously. This is not to say that the software downloads start and end exactly at the same time for each bed 12a-12n, just that the software download is initiated at the same time by selection of button 166. Screen 150 has a Cancel icon or button 168 that is selected by the user if it is decided that none of the beds 12a-12n listed in table 152 are to be upgraded with new operating software. After selection of Cancel icon 168, screen 150 is replaced by some other screen, such as a Home screen or other administration screen (not shown) in some embodiments.

Considering the specific example shown in FIG. 4, bed 12a and bed 12b which have the associated information shown in the first two rows of table 152, each are currently operating using bed operating software version 1.0 and can be upgraded so as to operate according to software version 2.0 as indicated in the two upper cells of column 162. Accordingly, the selections in column 164 for the upper two cells is "Upgrade" so that beds 12a and 12b will be upgraded to the version 2.0 bed operating software in response to selection of button 166 by the user. On the other hand, bed 12c, which is the same type of bed as indicated in column 156 as beds 12a, 12b, is already operating according to bed operating software version 2.0 and there is no new version of software to which bed 12c can be upgraded. Thus, the cell in column 162 corresponding to bed 12c has dashes, or is left blank or has some other null indicator in the cell, to indicate that there is no available software version for upgrading bed 12c. Accordingly, the cell in column 164 corresponding to bed 12c defaults to the "Don't Upgrade" option.

In some embodiments, subsequent selections of the cell in column 164 corresponding to bed 12c have no effect since there is no available software for bed 12c to be upgraded. That is, the "Don't Upgrade" option will persist in the cell despite subsequent selection of that particular cell by the user. As to bed 12n, table 152 indicates in column 156 that it is a "Type 2" bed and so bed 12n is not the same type (e.g., same make and/or model) as beds 12a, 12b, 12c. Furthermore, the current version of bed operating software for bed 12*n* is version 6.0 as indicated in column 160 of table 152 and the upgrade software version listed in column 162 for bed 12*n* is version 7.0. Thus, FIG. 4 suggests that bed 12*n* may be an older bed than the Type 1 beds 12*a*, 12*b*, 12*c* since its software version is a higher number version of software. In column 164, the cell associated with bed 12*n* has the "Upgrade" option selected. Thus, when button 166 is selected, bed 12*n* will be upgraded with the version 7.0 bed operating software for Type 2 beds while beds 12*a*, 12*b* will be upgraded with version 2.0 bed operating software for Type 1 beds. Accordingly, it is contemplated by this disclosure that different types of beds are upgraded with respective different software versions simultaneously via selection of button 166.

Figure 5:
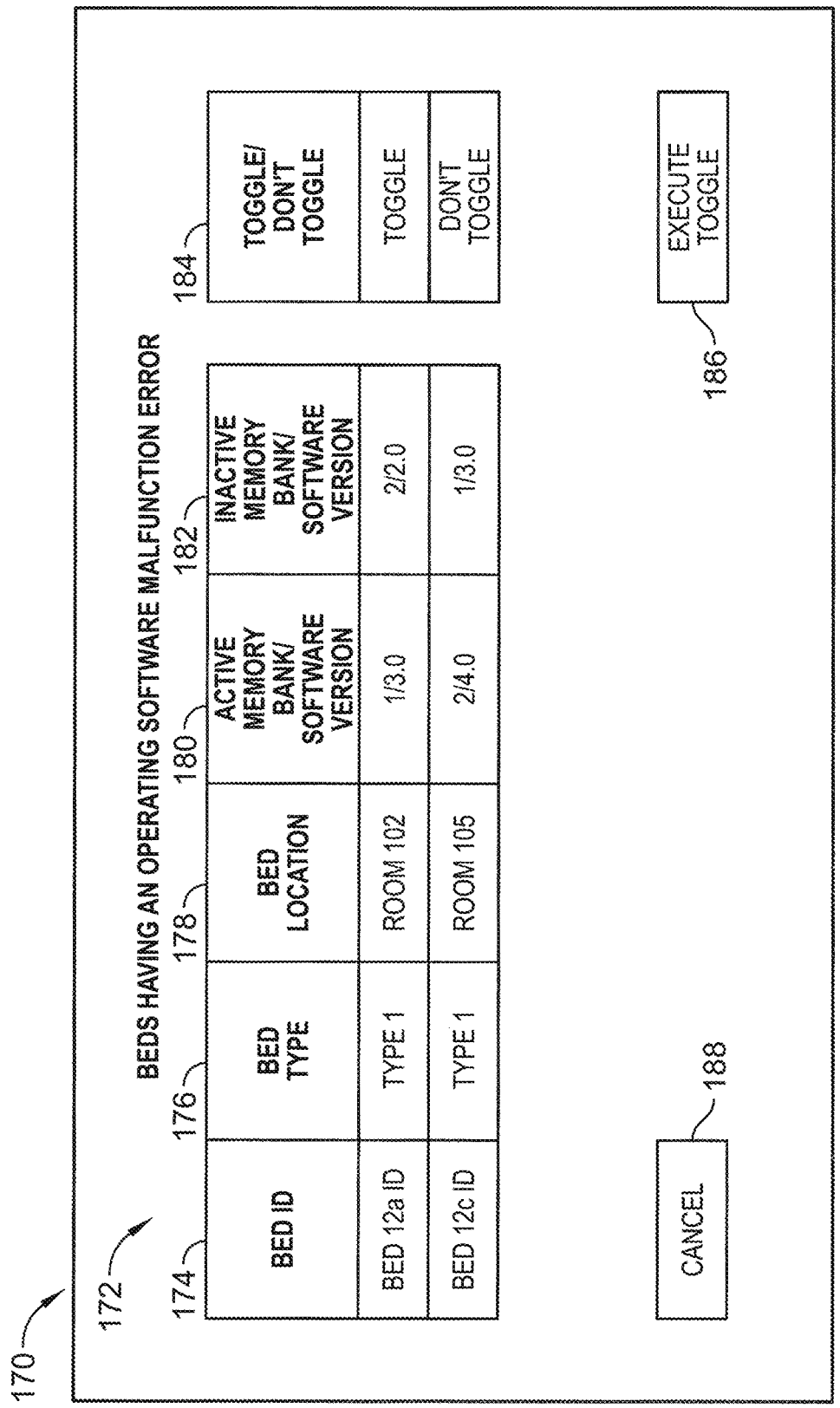
FIG. 5 is a screen shot of a remote toggle screen showing a list of beds that have experienced operating software malfunction errors, showing the software versions that are stored in the active and inactive memory banks for each of the listed beds, and showing a set of selection icons or buttons for selecting whether to toggle the memory banks so that the inactive memory bank becomes the active memory bank for the respective bed resulting in a different bed operating software version becoming active for the respective bed.

Referring now to FIG. 5, an illustrative example of a remote toggle screen 170 which appears on the display screen of the upgrade server 22 and/or remote upgrade computer 23 and which is used by a user to toggle between the active and inactive memory banks 111, 113 for beds experiencing operating software malfunction errors is shown. Screen 170 includes a table 172 having a first column 174 that lists the bed identification codes (bed ID's) of the beds 12*a*-12*n* that are in communication with server 22 and that have experienced one or more bed operating software malfunction errors. In the illustrative example, beds 12*a* and 12*c* have experienced such errors. As alluded to above, the errors in the bed operating software that are considered to be malfunction errors are those of sufficient magnitude to affect the operation of the associated bed to such an extent that the version of operating software should be changed. Thus, in some embodiments, noncritical or minor errors that may occur during execution of the bed operating software may not be considered to be of sufficient magnitude to warrant a designation as a malfunction error.

Still referring to FIG. 5, table 172 also includes a second column 176 that lists the bed type of the beds 12*a*-12*n* that are in communication with server 22 and that have experienced malfunction errors and a third column 178 that lists the location of each of beds 12*a*-12*n* that are in communication with server 22 and that have experienced malfunction errors. Table 172 also has a fourth column 180 and a fifth column 182 that lists the versions of bed operating software that are currently stored in the active and inactive memory banks 111, 113, respectively, of the respective beds in table 172. In the illustrative example of FIG. 5, bed 12*a* has memory bank 111 (i.e., the first memory bank or memory bank 1) as its active memory bank with version 3.0 being the bed operating software version in which one or more malfunction errors have occurred as indicated in column 180 and bed 12*a* has memory bank 113 (i.e., the second memory bank or memory bank 2) as its inactive memory bank with version 2.0 being the prior version of bed operating software stored therein as indicated in column 182. Also in the illustrative example, bed 12*c* has memory bank 113 (i.e., the second memory bank or memory bank 2) as its active memory bank with version 4.0 being the bed operating software version in which one or more malfunction errors have occurred as indicated in column 180 and bed 12*c* has memory bank 111 (i.e., the first memory bank or memory bank 1) as its inactive memory bank with version 3.0 being the prior version of bed operating software stored therein as indicated in column 182.

Screen 170 also has a separate Toggle/Don't Toggle column 184 to the right of table 172 that indicates, for each bed 12*a*-12*n* in table 172 (e.g., beds 12*a*, 12*c* in the illustrative example), whether the particular bed 12*a*-12*n* is to have its operating software version toggled to the version stored in the inactive memory bank listed in column 182. Each cell in column 184 can be selected by a user sequentially to switch between the "Toggle" and "Don't Toggle" options. Thus, if a cell in column 184 has the text "Toggle" shown in it, then a subsequent selection of that cell will change the selection to "Don't Toggle" and vice versa. If the display screen of the upgrade server 22 or computer 23 on which screen 170 is displayed is a touchscreen, then the user can simply touch each cell in column 184, as desired, to switch between the "Toggle" and "Don't Toggle" options. Alternatively or additionally, the user can click on each cell in column 184 with a cursor controlled by a computer mouse, for example, or use arrow keys to move a cursor to the desired cell and then pressing an enter key, to switch between the two options. It should be appreciated that column 184 may just as well use the terms other than "Toggle" and "Don't Toggle" but that have a similar meaning.

In the illustrative example, bed 12*c* has the "Don't Toggle" option selected because software version 3.0 in the inactive memory bank 111 of bed 12*c* is the same software version 3.0 in the active memory bank 111 of bed 12*a* which has experienced a malfunction error while operating in bed 12*a*. Thus, the user has decided not to toggle over to a software version for bed 12*c* that is a version which has proven in bed 12*a*, to already have a malfunction error.

Screen 170 has an Execute Toggle button or icon 186 that is selected by the user after the desired Toggle/Don't Toggle selections have been made in column 184 for each listed bed 12*a*-12*n* in table 174 if the user wants to proceed with toggling or switching the memory banks 111, 113 between active and inactive states so that the bed operating software in the inactive memory bank 111, 113, as the case may be, becomes the active bed operating software. In response to selection of button 186, server 22 transmits to each bed 12*a*-12*n* having the "Toggle" option selected in column 184, a message or instruction to switch or toggle the memory banks 111, 113 between the active and inactive states. Thus, the beds 12*a*-12*n* having the "Toggle" option selected are each toggled simultaneously. This is not to say that the toggling of memory banks 111, 113 start and end exactly at the same time for each bed 12*a*-12*n*, just that the toggling is initiated at the same time by selection of button 186. Screen 170 has a Cancel icon or button 188 that is selected by the user if it is decided that none of the beds 12*a*-12*n* listed in table 172 are to have their memory banks 111, 113 toggled or switched between the active and inactive states. After selection of Cancel icon 188, screen 170 is replaced by some other screen, such as a Home screen or other administration screen (not shown) in some embodiments.

Although certain illustrative embodiments have been described in detail above, variations and modifications exist within the scope and spirit of this disclosure as described and as defined in the following claims.

The invention claimed is:

1. A patient bed for use with a network including a remote computer, the patient bed comprising
 a bed frame to support a patient,
 bed circuitry carried by the bed frame, the bed circuitry being configured to receive a new version of bed operating software from the remote computer, the bed circuitry including a first memory bank and a second memory bank, one of the first and second memory banks storing therein a current version of bed operating software, the other of the first and second memory banks storing therein the new version of bed operating software received from the remote computer, whereby two versions of bed operating software is stored in the bed circuitry, wherein the bed circuitry is programmed with a memory toggle that is used to select between the first and second memory banks thereby to select which version of bed operating software is used to operate the patient bed, a touchscreen display carried by the bed frame and coupled to the bed circuitry, and a user input viewable on the touchscreen display, the user input being touchable on the graphical display screen to manually switch the memory toggle so that a user is able to select which of the software versions stored in the first and second memory banks is used to operate the patient bed, wherein the memory toggle of the patient bed is also switchable in response to receiving a signal from the remote computer that is transmitted to the patient bed in response to an input at the remote computer, which input at the remote computer also results in signals being transmitted to other patient beds, at least one of which is a different bed type than the patient bed, to switch respective memory toggles of the other patient beds, wherein the memory toggle comprises a toggle flag that is used at start-up of the patient bed to determine which of the first and second memory banks is currently active.

2. The patient bed of claim 1, wherein the first and second memory banks each comprise flash memory banks that are independent of each other.

3. The patient bed of claim 1, wherein the new version of bed operating software received from the remote computer is stored at download into whichever of the first and second memory banks is inactive.

4. The patient bed of claim 3, wherein upon next start-up of the patient bed, the memory toggle is switched so that a previously active memory bank of the first and second memory banks becomes inactive and so that a previously inactive memory bank of the first and second memory banks becomes active.

5. The patient bed of claim 3, wherein during download of the new version of bed operating software into the inactive memory bank, the patient bed continues to be operated according to the current version of bed operating software stored in the active memory bank.

6. The patient bed of claim 1, wherein after the patient bed is operated according to the new version of the bed operating software, the bed circuitry is programmed to automatically switch the memory toggle if an error occurs in the new version of bed operating software so that the prior version of bed operating software is once again used to operate the patient bed.

7. The patient bed of claim 1, wherein the remote computer is usable to download the new version of operating software to the patient bed while also downloading other new versions of operating software to the other patient beds.

8. A system comprising a computer, and a plurality of patient beds that are remote from the computer and that include at least two different bed types, each patient bed comprising a bed frame to support a patient, bed circuitry carried by the bed frame, and a touchscreen display carried by the bed frame and coupled to the bed circuitry, the bed circuitry of each bed being configured to receive a new version of bed operating software from the computer, the bed circuitry including a first memory bank and a second memory bank, one of the first and second memory banks storing therein a current version of bed operating software for each bed, the other of the first and second memory banks storing therein the new version of bed operating software received from the remote computer, whereby two versions of bed operating software is stored in the bed circuitry of each bed, wherein the computer is configured to upgrade the plurality of patient beds with the new version of bed operating software simultaneously, wherein the computer is configured to permit a user to select which of the plurality of patient beds is to be upgraded with the new version of bed operating software and to deselect others of the patient beds that are not to be upgraded, wherein the bed circuitry of each patient bed is programmed with a memory toggle that is used to select between the first and second memory banks thereby to select which version of bed operating software is used to operate the respective patient bed, wherein respective user inputs are viewable on the touchscreen displays of each of the patient beds, the respective user inputs being touchable on the corresponding touchscreen display to manually switch the memory toggle of the respective patient bed so that the user is able to select which of the software versions stored in the first and second memory banks of the respective bed is used to operate the respective patient bed, wherein the computer is also configured to receive an input from the user to remotely and simultaneously send signals to switch the memory toggles of the plurality of patient beds, wherein the memory toggle of each patient bed comprises a toggle flag that is used at start-up of the respective patient bed to determine which of the first and second memory banks is currently active.

9. The system of claim 8, wherein the computer is configured to display a list of each of the plurality of patient beds that is available for upgrade.

10. The system of claim 8, wherein each of the patient beds that are available for upgrade register with the computer.

11. The system of claim 10, wherein each of the patient beds that register with the computer transmits a bed identification (ID) and a software version number of the current bed operating software for the respective patient bed.

12. The system of claim 8, wherein the computer displays a table in which the user designates which of the plurality of patient beds is to be upgraded with the new version of bed operating software and to deselect the others of the patient beds that are not to be upgraded.

13. The system of claim 8, wherein the first and second memory banks of each patient bed each comprise flash memory banks that are independent of each other.

14. The system of claim 8, wherein the new version of bed operating software received from the remote computer by each patient bed is stored at download into whichever of the first and second memory banks is inactive in the respective patient bed.

15. The system of claim 14, wherein upon next start-up of each of the patient beds, the memory toggle is switched so that a previously active memory bank of the first and second memory banks becomes inactive and so that a previously inactive memory bank of the first and second memory banks becomes active.

16. The system of claim 14, wherein during download of the new version of bed operating software into the inactive memory bank of each patient bed, each of the patient beds continue to be operated according to the current version of bed operating software stored in the active memory bank of the respective patient bed.

17. The system of claim 8, wherein after each of the patient beds is operated according to the new version of the bed operating software, the respective bed circuitry is programmed to automatically switch the memory toggle if an error occurs in the new version of bed operating software so that the prior version of bed operating software is once again used to operate the respective patient bed.

18. A system comprising
a computer, and
a plurality of patient beds that are remote from the computer and that include at least two different bed types, each patient bed comprising a bed frame to support a patient, bed circuitry carried by the bed frame, and a touchscreen display carried by the bed frame and coupled to the bed circuitry, the bed circuitry of each bed being configured to receive a new version of bed operating software from the computer, the bed circuitry including a first memory bank and a second memory bank, one of the first and second memory banks storing therein a current version of bed operating software for each bed, the other of the first and second memory banks storing therein the new version of bed operating software received from the remote computer, whereby two versions of bed operating software is stored in the bed circuitry of each bed, wherein the computer is configured to upgrade the plurality of patient beds with the new version of bed operating software simultaneously, wherein the computer is configured to permit a user to select which of the plurality of patient beds is to be upgraded with the new version of bed operating software and to deselect others of the patient beds that are not to be upgraded, wherein the bed circuitry of each patient bed is programmed with a memory toggle that is used to select between the first and second memory banks thereby to select which version of bed operating software is used to operate the respective patient bed, wherein respective user inputs are viewable on the touchscreen displays of each of the patient beds, the respective user inputs being touchable on the corresponding touchscreen display to manually switch the memory toggle of the respective patient bed so that the user is able to select which of the software versions stored in the first and second memory banks of the respective bed is used to operate the respective patient bed, wherein the computer is also configured to receive an input from the user to remotely and simultaneously send signals to switch the memory toggles of the plurality of patient beds, wherein the remote computer is configured to display which of the first and second memory banks of the plurality of patient beds is active and which is inactive.

19. The patient bed of claim 1, further comprising a barrier coupled to the frame and configured to block egress of the patient from the frame and wherein the touchscreen display is mounted to the barrier.

20. The patient bed of claim 19, wherein the barrier comprises a siderail.

21. The system of claim 8, wherein each patient bed further comprises a barrier coupled to the respective bed frame and configured to block egress of the corresponding patient from the respective bed frame and wherein each touchscreen display is mounted to the respective barrier.

22. The system of claim 21, wherein each barrier comprises a siderail.

* * * * *